(12) United States Patent
Pescatore et al.

(10) Patent No.: US 7,066,646 B2
(45) Date of Patent: Jun. 27, 2006

(54) PROCESS AND APPARATUS FOR CALIBRATION OF A RADIOLOGICAL IMAGING DEVICE

(75) Inventors: Jérémie Pescatore, Paris (FR); Cyril Riddell, Paris (FR); Yves Trousset, Palaiseau (FR); Régis Vaillant, Villebon sur Yvette (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 51 days.

(21) Appl. No.: 10/737,078

(22) Filed: Dec. 16, 2003

(65) Prior Publication Data

US 2004/0202288 A1 Oct. 14, 2004

(30) Foreign Application Priority Data

Dec. 18, 2002 (FR) .................................. 02 16078

(51) Int. Cl.
*G01D 18/00* (2006.01)

(52) U.S. Cl. .................. 378/207; 378/18; 250/252.1

(58) Field of Classification Search ............... 378/207, 378/4–20, 163–164; 250/252.1, 363.09
See application file for complete search history.

(56) References Cited

U.S. PATENT DOCUMENTS

| | | | |
|---|---|---|---|
| 4,352,020 A | 9/1982 | Horiba et al. | |
| 5,214,578 A | 5/1993 | Cornuejols et al. | |
| 5,442,674 A | 8/1995 | Picard et al. | |
| 5,963,612 A * | 10/1999 | Navab | 378/4 |
| 6,285,902 B1 * | 9/2001 | Kienzle et al. | 600/427 |
| 6,379,043 B1 * | 4/2002 | Zylka et al. | 378/207 |
| 6,652,142 B1 * | 11/2003 | Launay et al. | 378/205 |
| 2002/0163996 A1 | 11/2002 | Kerrien et al. | |

FOREIGN PATENT DOCUMENTS

| | | |
|---|---|---|
| EP | 0343600 A1 | 11/1989 |
| EP | 1081647 A1 | 3/2001 |
| FR | 2823968 A1 | 10/2002 |

* cited by examiner

*Primary Examiner*—Edward J. Glick
*Assistant Examiner*—Jurie Yun
(74) *Attorney, Agent, or Firm*—Cantor Colburn LLP

(57) ABSTRACT

In the field of medical imaging minimizing the number of acquisitions required to calibrate a radiological device. Calibration of the radiological imaging device is provided by moving the device with respect to a calibration object and performing a series of acquisitions, each acquisition being associated to a calibration position of the device. Based on the acquisitions performed, determining the projection parameters associated to each calibration position of the device. For an additional position that has not been taken by the device during the acquisition, determining the projection parameter values associated to this additional position according to the parameters associated to the calibration positions.

38 Claims, 4 Drawing Sheets

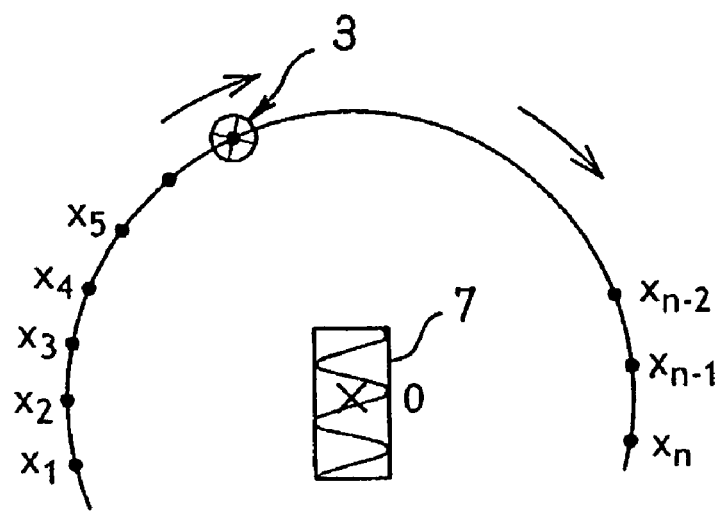
FIG_3
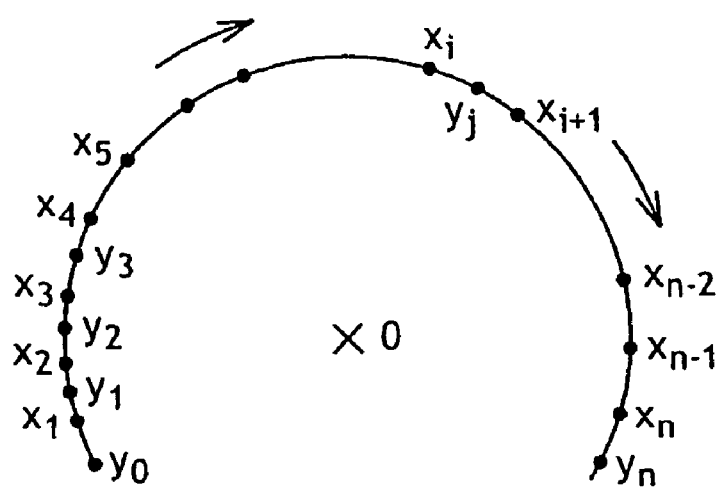
FIG_4

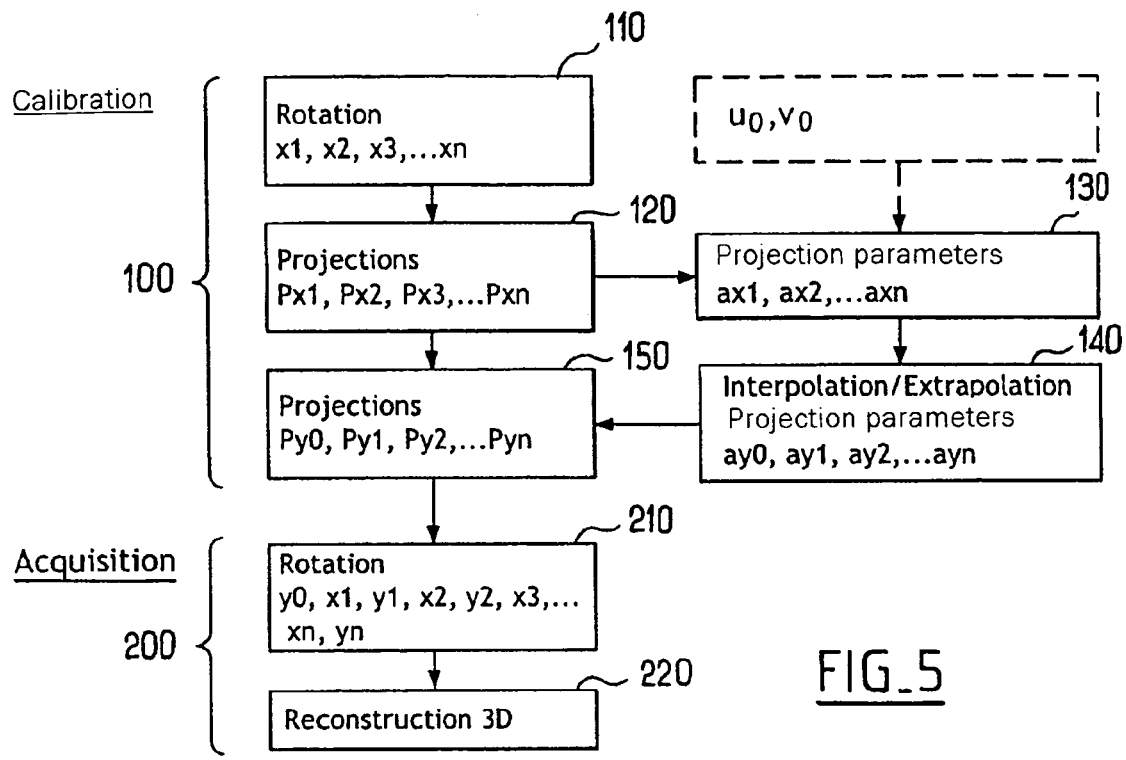
FIG_5
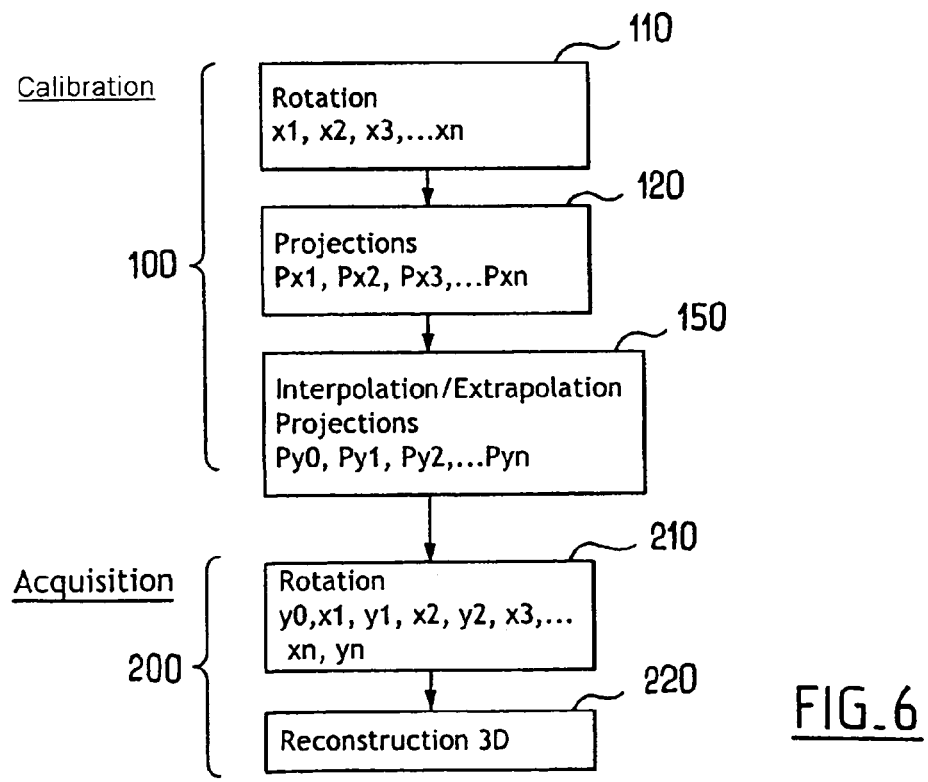
FIG_6

PROCESS AND APPARATUS FOR CALIBRATION OF A RADIOLOGICAL IMAGING DEVICE

CROSS-REFERENCE TO RELATED APPLICATIONS

This application claims a benefit of a priority under 35 USC 119(a)–(d) to French Patent Application No. 02 16078 filed Dec. 18, 2002, the entire contents of which are hereby incorporated by reference.

BACKGROUND OF THE INVENTION

This invention and embodiments thereof is directed to a medical field, and more particularly the field of radiological imaging devices. These devices comprise means for emitting radiation, such as an X ray source, and means for acquiring an image, such as an image detector, mounted on the end of a C shaped arm, and the object of which the image is to be taken is placed between the two sides of the arm. The images acquired by the detector as the arm rotates around the object, and thus several acquisitions correspond to different points of view of the object. Means for processing allow a three-dimensional model of the object to be reconstructed from the acquired two-dimensional images. This reconstruction supposes that the different positions of the device are known precisely as well as its geometric characteristics.

The three-dimensional model obtained can be used by a medical practitioner, such as a surgeon, before an operation in order to become familiar with the part of the anatomy for which the operation is intended. The three-dimensional model can also be used during the operation. For this, the medical practitioner disposes of equipment that allows the two-dimensional views of the part of the anatomy to be displayed in real time, these views being calculated from the three dimensional model.

The reconstruction of the three-dimensional model requires the imaging device to be "geometrically calibrated" beforehand. This calibration allows the three dimensional space to be linked to the two dimensional information provided by the various two dimensional projections. If the calibration is imprecise, then the quality of the three dimensional model reconstructed will reflect these imperfections.

A known calibration technique comprises placing markers inside an X ray field, positioned on a ghost image that act as markers in space, and carrying out a series of acquisitions. As the position of these markers in the three dimensional space is known, then the geometry of the acquisition can be deduced for each projection by inversion of a system of equations derived from the position of the markers on the projected images. A technique of this type is described, for example, in U.S. Pat. No. 5,442,674.

In general, when an image is taken of a part of the anatomy, the device is commanded to perform a series of acquisitions in the same geometrical conditions as the series of calibration acquisitions, so that the geometry of each acquisition is known precisely. This is possible due to the fact that the movements of the C shaped arm can be repeated.

If, however, the acquisitions of the part of the anatomy are not carried out in the same geometrical conditions as the calibration acquisitions (number of views, angular positions, speed of rotation, initial and final positions), then a new calibration has to be performed, which increases the number of views taken for the calibration.

Furthermore, the number of acquisitions required to obtain a good quality three-dimensional model depends on the type of anatomical structure to be imaged. Typically, the three dimensional reconstruction of the bone structures requires approximately 120 views whereas the three dimensional reconstruction of a blood vessel requires approximately 40 views.

The result is that as many calibration acquisitions as possible must always be taken so that the calibration is valid for imaging any type of structure.

BRIEF DESCRIPTION OF THE INVENTION

An embodiment of the invention is directed to minimizing the number of acquisitions required to calibrate the device. An embodiment of the invention is directed to a process and apparatus for calibration of a radiological imaging device comprising a source and a detector comprising:

moving the device with respect to a calibration object and performing a series of acquisitions, each acquisition being associated to a calibration position of the device;

based on the acquisitions performed, determining the projection parameters associated to each calibration position of the device;

for an additional position that has not been taken by the device during the acquisition step, determining the projection parameter values associated to this additional position according to the parameters associated to the calibration positions.

BRIEF DESCRIPTION OF THE DRAWINGS

An embodiment of the invention will be better understood from the following description, which is given purely by way of illustration and is not restrictive, when read in conjunction with the appended figures in which:

FIG. 3 represents the different positions taken by the source during the calibration acquisitions;

FIG. 4 represents the additional positions that can be covered for the application of an embodiment of the process;

FIG. 5 is a block diagram schematically representing the different steps of an embodiment of the process;

FIG. 6 is a block diagram schematically representing the different steps of a variant of the embodiment of FIG. 5.

DETAILED DESCRIPTION OF THE INVENTION

Figure 1:
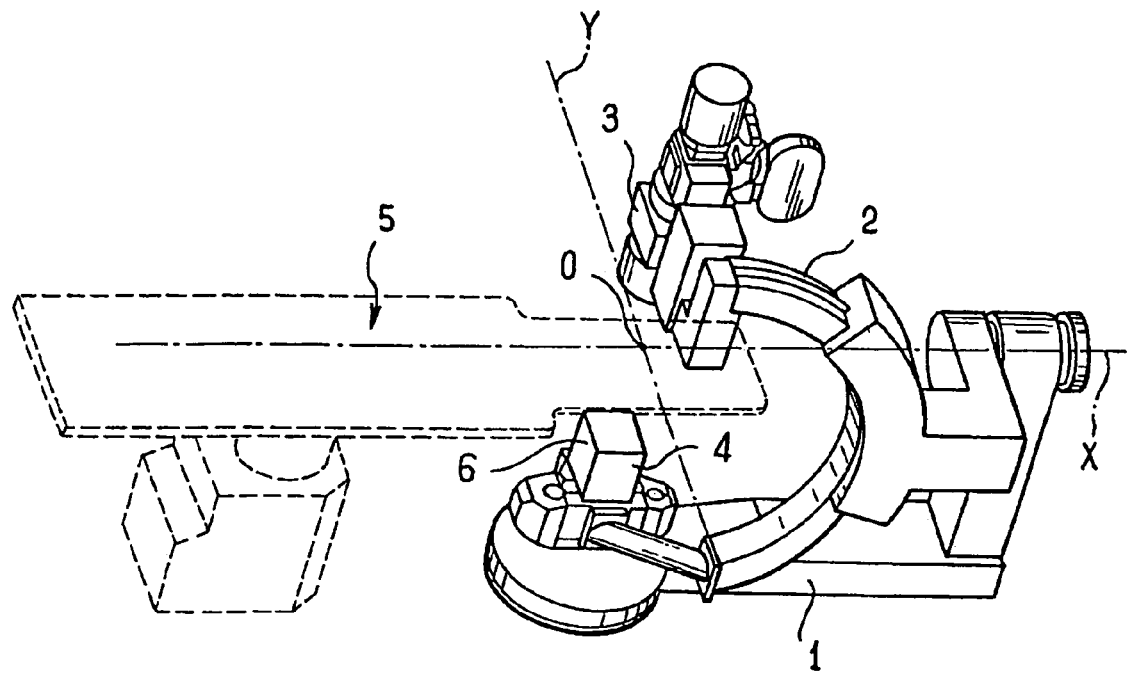
FIG. 1 represents diagrammatically a C shaped arm type-imaging device.

In FIG. 1, the imaging device comprises a base 1 fixed to the ground, and upon which a C shaped arm 2 is mounted. The C shaped arms supports at each of its ends a source 3 formed by an X ray tube and an image detector 4. These elements are disposed so that the focus of the source 3 and the plane 6 of the detector 4 are diametrically opposed on the C shaped arm. The device is positioned close to a table 5 on which a patient will be placed. The plane of the table 5 stretches between the two arms of the C shaped arm, which is to say between the source 3 and the detector 4. The C shaped arm 2 can be commanded in rotation around the X or Y axes, these two axes intersecting at a point O, the center of rotation of the C shaped arm.

During the calibration phase of the device, a ghost image comprising markers is positioned on the table 5 between the source 3 and the detector 4, more or less at the level of point O. During this phase, the C shaped arm is commanded in rotation and the device performs a series of n acquisitions. Each image acquired is a projection of the markers, of the three dimensional space towards the plane 6 of the detector 4.

Figure 2:
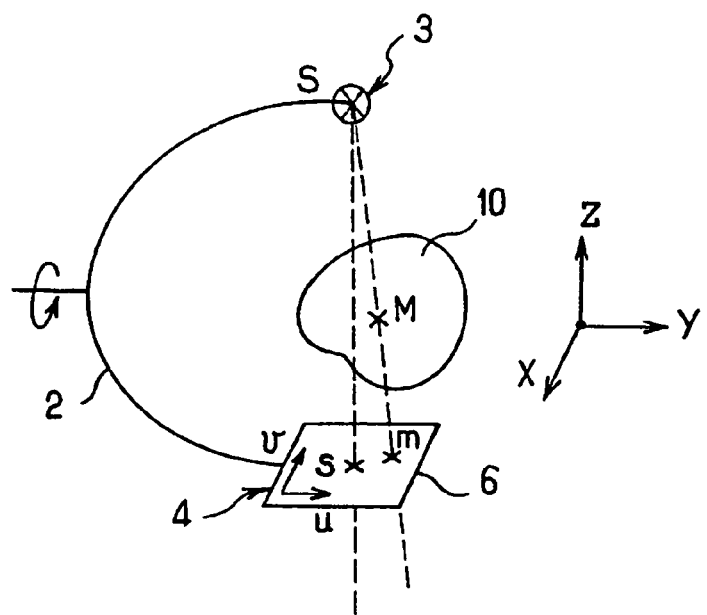
FIG. 2 represents diagrammatically a C shaped arm supporting a source and a detector.

In FIG. 2, the C shaped arm 2 is shown schematically, the focal point S of the source 3 and the plane 6 of the detector 4 as well as an object 10 of which a three dimensional model is to be made.

The geometrical acquisition parameters of the device are, for example, as follows: six extrinsic parameters (three translations, three rotations) that define the position in space of the C shaped arm in a three-dimensional reference (X, Y, Z); five intrinsic parameters defining the projection in the detector plane: two zoom factors ($\alpha_u$, $\alpha_v$) along two axes of a two dimensional reference (u, v) linked to the plane, the co-ordinates ($u_o$, $v_o$) of the projection s of the focal point S of the source 3, as well as a deviation angle that is generally considered as nil.

Take a point M of the object to be imaged of co-ordinates ($X_M$, $Y_M$, $Z_M$) in space and m its projected image of co-ordinates ($U_M$, $V_M$) in the detector plane. This gives:

$$\begin{bmatrix} su_m \\ sv_m \\ s \end{bmatrix} = P \cdot \begin{bmatrix} X_M \\ Y_M \\ Z_M \\ 1 \end{bmatrix} = \underbrace{\begin{bmatrix} \alpha_u & 0 & u_0 & 0 \\ 0 & \alpha_v & v_0 & 0 \\ 0 & 0 & 1 & 0 \end{bmatrix} - [R/T] -}_{P} \begin{bmatrix} X_M \\ Y_M \\ Z_M \\ 1 \end{bmatrix} \quad (1)$$

where R and T are the rotation and translation matrices that define the position of the C shaped arm in the three-dimensional reference (X, Y, Z) and s is a scale factor.

The projection matrix P is therefore a 3×4 matrix whose twelve coefficients are a result of combinations of the eleven parameters (six extrinsic parameters and five intrinsic parameters) and a scale factor.

FIG. 5 shows the different steps of a three-dimensional reconstruction process. This process comprises a calibration phase 100 beforehand and an acquisition phase 200 of the anatomical part to be imaged.

In step 110 of the calibration phase, a ghost image is positioned on the table and the C shaped arm is driven in rotation.

FIG. 3 represents the different positions $x_1$, $x_2$, $x_n$, views taken by the source 3 around the ghost image 7 during the series of calibration acquisitions.

In step 120 represented in FIG. 5, means for processing calculate for each position $X_1$, $X_2$, $X_3$, ... $X_n$, of the source 3 a projection matrix PX (defined by the relation (1) above). The projection P, associated to a position $x_1$ of the source is determined from the configuration of the markers on the image acquired, the position of the markers in space is known.

A calibration algorithm used by the means for processing allows each calibration position $X_1$, $X_2$, $X_3$, ... $X_n$ to be associated to a projection $PX_1$, $PX_2$, $PX_3$, ... $PX_n$.

In step 130, the means for calculation determine the geometrical parameters $a_{x1}$, $a_{x2}$, ... $a_{xn}$ of the device acquisition. For each projection $P_{x1}$, there are eleven of these parameters $a_{x1}$ (six extrinsic parameters and five intrinsic parameters, as previously defined).

In step 140, the means for processing estimate geometrical acquisition parameters $a_{y1}$, $a_{y2}$, ... $a_{ym-1}$, for these additional positions $y_i$.

As well as being shown on FIG. 4, consider a series of additional positions $y_0$, $y_1$, $y_2$, ... $y_n$, spread over the trajectory of the source. The position $y_0$ is, for example, positioned before the $x_1$ position and the $y_n$ position is positioned after the $x_n$ position. Each position $y_i$ (i=1 ... n−1) is located on the source trajectory between two successive calibration positions $x_i$ and $x_{i+1}$ (i<n)

The estimation of the geometrical acquisition parameters $a_{y1}$, $a_{y2}$, ... $a_{ym-1}$, is possible given that the source trajectory is continuous. The result is that the variation of the acquisition parameters is also continuous.

The means for processing carry out an interpolation of the geometrical parameters $a_{x1}$, $a_{x2}$ ... $a_{xn}$ determined for the x, $x_2$, ... $x_n$ positions. Each geometrical parameter $a_{y1}$ is therefore a combination of the $a_{xi}$ parameters:

$$a_{yj} = \sum_{i=1}^{n} c_{ij} \times a_{xi}$$

This interpolation will only take account of a limited number of calibration positions, less than five. For example, the means for processing can only take into account the two source positions $x_i$ and $x_{i+1}$ that directly surround the $y_i$ position. For the $y_o$ and $y_n$ extreme positions, the means for processing perform an extrapolation of the geometrical parameters $a_{x1}$, $a_{x2}$, ... $a_{xn}$ determined for the $x_1$, $x_2$, ... $x_n$, positions. In the same way, this extrapolation will only take account of a limited number of calibration positions, less than five. For example, the means for processing can only take into account the two source positions $x_i$ and $x_{i+1}$ that are closest to the $y_i$ position.

The interpolations and extrapolations carried out from two positions may be advantageously linear. For a greater number of positions to be taken into account, the interpolation functions can be polynomial, rational or another type of function.

In step 150, the means for processing deduct from these parameters the $Py_1$, $Py_2$, ... $Py_n$ projection matrices associated to the additional positions $y_0$, $y_1$, $y_2$, ..., $y_n$.

The effect of the calibration phase 100 is to increase the number of calibration positions obtained with respect to the initial number n of acquisition positions. The imaging device is then commanded during the acquisition phase 200 to create an image of the anatomic structure of a patient.

In step 210, a patient is positioned on the table and the C shaped arm is driven in rotation. The image acquisition can be carried out for all or part of the calibration positions $y_0$, $x_1$, $x_2$, $y_2$, $x_3$, ... $x_n$, $y_n$ of the source.

In step, 220, the means for processing reconstruct a three dimensional model of the anatomic structures of the patient from the images acquired and the projections $P_{x1}$, $P_{y1}$, $P_{x2}$, $P_{y2}$, $P_{x3}$, ..., $P_{yn}$, $P_{xn}$, associated to these images. FIG. 6 shows a variant of the three-dimensional reconstruction procedure of FIG. 5.

The process is similar to that of FIG. 5 except that the coefficients $p_{y0}$, $P_{y1}$, ..., $p_{yn}$, of the projection matrices $p_{y0}$, $p_{y1}$, ..., $p_{yn}$, are directly determined by interpolation or extrapolation of the coefficients $p_{x1}$, $p_{x2}$, ..., $p_{xn}$, of the $p_{y0}$, $p_{y1}$, ..., $p_{yn}$, matrices.

Thus at step 150, the means for processing perform an interpolation of the matrices $p_{x1}$, $p_{x2}$, $p_{x3}$, ..., $p_{xn}$, determined for the positions $x_1$, $x_2$, $x_3$, ..., $x_n$ at step 120. Each $P_y$ matrix is therefore a combination of the $P_x$ matrices:

$$Py_j = \sum_{i=1}^{n} C_{ij} \times Px_i$$

In the same way as above, this interpolation can only take into account a limited number of calibration positions, less than five. For example, the means for processing can only take into account the two source positions $x_i$ and $x_{i+1}$ that directly surround the $y_i$ position. For the $y_o$ and $y_n$ extreme positions, the means for processing perform an extrapolation of the geometrical parameters $a_{x1}$, $a_{x2}$, ... $a_{xn}$ determined for the $x_1$, $x_2$, ... $x_n$, positions. In the same way, this extrapolation will only take account of a limited number of calibration positions, less than five. For example, the means for processing can only take into account the two source positions $x_i$ and $x_{i+1}$ that are closest to the $y_i$ position.

The interpolations and extrapolations carried out from two positions may be linear.

The variant of the image reconstruction process shown in FIG. 6 does not require step 130 for calculating the geometrical projection parameters, as the interpolation is carried out directly from the projection matrices $p_{x1}$, $p_{x2}$, $p_{x3}$, ..., $p_{ym}$, determined during calibration. Consequently, this variant is simplified in comparison to the process of FIG. 5, which means that the processing time is shorter.

However, the process shown in FIG. 5 permits access to the geometrical parameters $a_{x1}$, $a_{x2}$, ..., $a_{xn}$. In particular, this process allows these parameters to be smoothed out. Therefore as shown in dotted lines in FIG. 5, it is possible to impose constraints on certain parameters taken into account by the calibration algorithm permitting the geometrical calibration acquisition parameters to be determined.

For example, a law is imposed defining certain of the parameters taken into account by the algorithm. This law may comprise setting certain parameters or defining them by a more complex function dependent on information known beforehand and/or other geometrical projection parameters. For example, it can be imposed that the position of the projection of the source s is always in the center of the detector, which is the equivalent of setting $(u_0, v_0)$. It is also possible to set the focal distance between the focal point of the source, which is the equivalent of setting the zoom factors $(\alpha_u, \alpha_v)$.

The setting of one or more of these parameters can make the results obtained more regular and consequently eliminate the parasites they contain.

Figure 7:
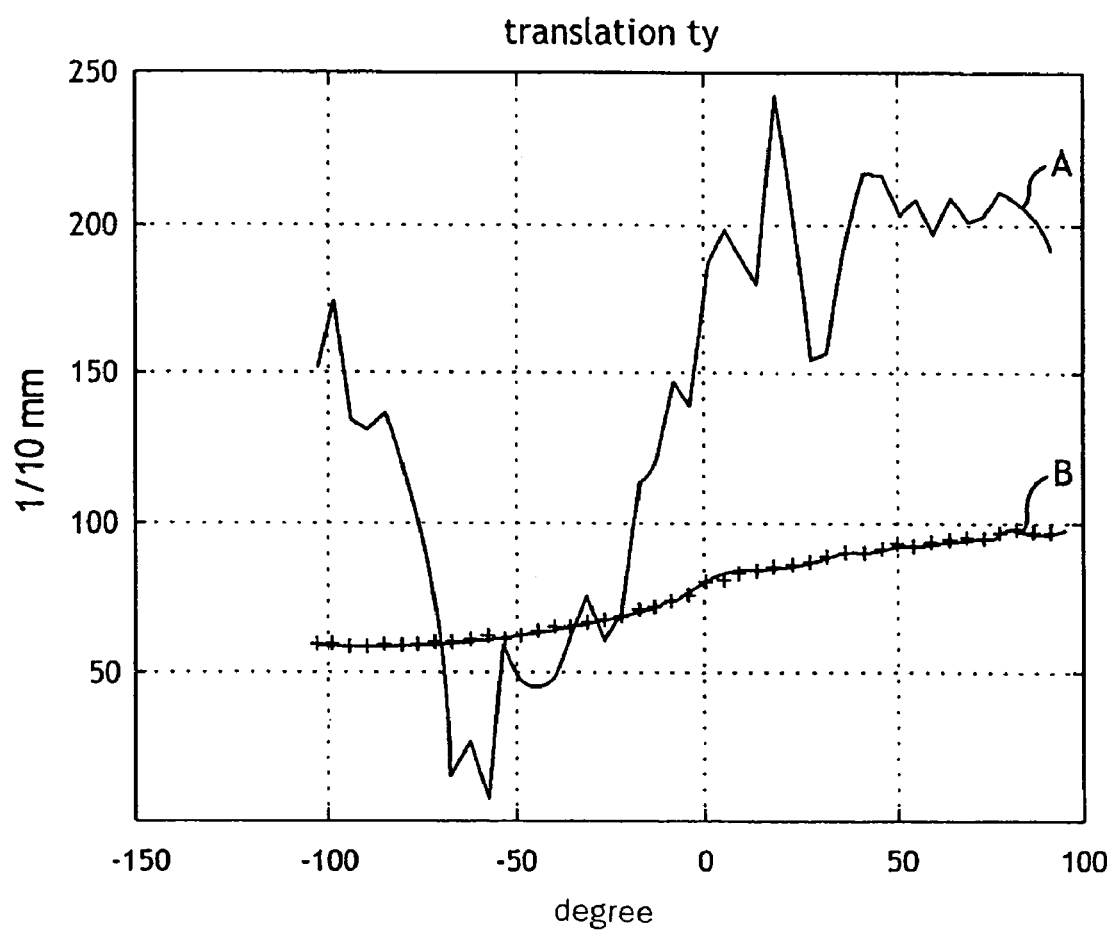
FIG. 7 is a graph illustrating the result after smoothing of the projection parameters calculated by an embodiment of the process.

FIG. 7 illustrates the variation of a coefficient $t_y$ of the T matrix defining the translation of the C shaped arm along the y axis for a group of positions defined by the angle of rotation of the C shaped arm. Curve A represents the results obtained when no geometrical parameters are set. Curve B represents the results obtained when the parameters $(u_0, v_0)$ have been set.

The described reconstruction process allows the projection parameters to be calculated for additional source positions for which there has been no calibration acquisition carried out. There can, be any number of additional positions and situated anywhere on the trajectory of the source depending on the requirements of the final three-dimensional reconstruction. In particular, it is possible to insert as many additional $y_1$ positions between the $x_1$ calibration positions as required.

This process can be applied to any number of additional positions, different from the calibration positions. The effect of this is to multiply by calculation the number of calibration positions obtained. Consequently, this process makes it possible to carry out just a limited number of acquisitions. Furthermore, this process avoids having to carry out new calibration acquisitions in the event of the number of acquisitions performed being insufficient. The projection parameters can be geometrical parameters characteristic of the position of the device in space (extrinsic parameters) or geometrical parameters characteristic of the source and the detector (intrinsic parameters). These parameters can also be coefficients of a global matrix that defines the projection of an object in the three dimensional space in the plane of the detector.

One skilled in the art may make or propose various modifications to the structure/way and/or function and/or result for the disclosed embodiments and equivalents thereof without departing from the scope and extant of the invention.

What is claimed is:

1. A process for calibration of a radiological imaging device comprising:
    moving the device with respect to a calibration object and performing a series of acquisitions, each acquisition being associated to a calibration position of the device;
    based on the acquisitions performed, determining the projection parameters associated to each calibration position of the device;
    for an additional position that has not been taken by the device during the acquisition step, determining the projection parameter values associated to this additional position according to the parameters associated to the calibration positions.

2. The process according to claim 1 wherein the projection parameters comprise geometrical parameters that are characteristic of the positioning of the device in space.

3. The process according to claim 2 wherein the projection parameters comprise geometrical parameters that are characteristic of means for emitting radiation and means for acquiring an image.

4. The process according to claim 3 wherein the projection parameters include coefficients of a global matrix that defines the projection of an object in the three dimensional space in a plane of the means for acquiring an image.

5. The process according to claim 3 wherein the projection parameters associated to the additional position are determined by an interpolation or extrapolation law of the projection parameters associated to the calibration positions.

6. The process according to claim 5 wherein the interpolation law is linear, polynomial or rational.

7. The process according to claim 6 wherein to projection parameters associated to the additional position are determined by a combination of the projection parameters associated to the calibration positions of the device closest to the additional position, the number of positions taken into account being less than five.

8. The process according to claim 6 wherein during the step where the projection parameters associated to each device calibration position are determined, some of the projection parameters are defined by a law dependent on information known beforehand and/or other geometrical projection parameters.

9. The process according to claim 3 wherein the projection parameters associated to the additional position are determined by a combination of the projection parameters associated to the calibration positions of the device closest to the additional position, the number of positions taken into account being less than five.

10. The process according to claim 3 wherein during the step where the projection parameters associated to each device calibration position are determined, some of the projection parameters are defined by a law dependent on information known beforehand and/or other geometrical projection parameters.

11. The process according to claim 2 wherein the projection parameters include coefficients of a global matrix that defines the projection of an object in the three dimensional space in a plane of the means for acquiring an image.

12. The process according to claim 2 wherein the projection parameters associated to the additional position are determined by an interpolation or extrapolation law of the projection parameters associated to the calibration positions.

13. The process according to claim 12 wherein the interpolation law is linear, polynomial or rational.

14. The process according to claim 2 wherein the projection parameters associated to the additional position are determined by a combination of to projection parameters associated to the calibration positions of the device closest to the additional position, the number of positions taken into account being less than five.

15. The process according to claim 2 wherein during the step where the projection parameters associated to each device calibration position are determined, some of the projection parameters are defined by a law dependent on other geometrical projection parameter.

16. The process according to claim 1 wherein the projection parameters comprise geometrical parameters that are characteristic of means for emitting radiation and means for acquiring an image.

17. The process according to claim 16 wherein the projection parameters include coefficients of a global matrix that defines the projection of an object in the three dimensional space in a plane of the means for acquiring an image.

18. The process according to claim 16 wherein the projection parameters associated to the additional position are determined by an interpolation or extrapolation law of the projection parameters associated to the calibration positions.

19. The process according to claim 18 wherein the interpolation law is linear, polynomial or rational.

20. The process according to claim 16 wherein the projection parameters associated to the additional position are determined by a combination of the projection parameters associated to the calibration positions of the device closest to the additional position, the number of positions taken into account being less than five.

21. The process according to claim 16 wherein during the step where the projection parameters associated to each device calibration position are determined, some of the projection parameters are defined by a law dependent on information known beforehand and/or other geometrical projection parameters.

22. The process according to claim 1 wherein the projection parameters include coefficients of a global matrix that defines the projection of an object in the three dimensional space in a plane of the means for acquiring an image.

23. The process according to claim 22 wherein the projection parameters associated to the additional position are determined by an interpolation or extrapolation law of the projection parameters associated to the calibration positions.

24. The process according to claim 23 wherein the interpolation law is linear, polynomial or rational.

25. The process according to claim 22 wherein the projection parameters associated to the additional position are determined by a combination of the projection parameters associated to the calibration positions of the device closest to the additional position, the number of positions taken into account being less than five.

26. The process according to claim 22 wherein during the step where the projection parameters associated to each device calibration position are determined, some of the projection parameters are defined by a law dependent on information known beforehand and/or other geometrical projection parameters.

27. The process according to claim 1 wherein the projection parameters associated to the additional position are determined by an interpolation or extrapolation law of the projection parameters associated to the calibration positions.

28. The process according to claim 27 wherein the interpolation law is linear, polynomial or rational.

29. The process according to claim 27 wherein the projection parameters associated to the additional position are determined by a combination of the projection parameters associated to the calibration positions of the device closest to the additional position, the number of positions taken into account being less than five.

30. The process according to claim 27 wherein during the step where the projection parameters associated to each device calibration position are determined, some of the projection parameters are defined by a law dependent on information known beforehand and/or other geometrical projection parameters.

31. The process according to claim 1 wherein the projection parameters associated to the additional position arc determined by a combination of the projection parameters associated to the calibration positions of the device closest to the additional position, the number of positions taken Into account being less than five.

32. The process according to claim 31 wherein the number of positions taken into account is equal to 2.

33. The process according to claim 32 wherein during the step where the projection parameters associated to each device calibration position are determined, some of the projection parameters are defined by a law dependent on information known beforehand and/or other geometrical projection parameters.

34. The process according to claim 31 wherein during the step where the projection parameters associated to each device calibration position are determined, some of the projection parameters are defined by a law dependent on information known beforehand and/or other geometrical projection parameters.

35. The process according to claim 1 wherein during the step where the projection parameters associated to each device calibration position are determined, some of the projection parameters are defined by a law dependent on information known beforehand and other geometrical projection parameters.

36. A process for reconstruction a three dimensional model from acquired images from a device having means for emitting radiation comprising:
a calibration phase comprising:
moving the device with respect to a calibration object and performing a series of acquisitions, each acquisition being associated to a calibration position of the device;

based on the acquisitions performed, determining the projection parameters associated to each calibration position of the device;

for an additional position that ham not been taken by the device during the acquisition step, determining the projection parameter values associated to this additional position according to the parameters associated to the calibration positions;

an acquisition phase comprising:

moving the device with respect to an object to be imaged and carrying out a series of acquisitions, each acquisition being associated to a calibration position or an additional position of the means for emitting radiation; and reconstructing a three-dimensional model of the object from the images acquired and the associated projection parameters, determined during the calibration phase.

37. An apparatus for calibrating a radiological imaging device comprising:

means for emitting radiation;

means for providing a calibration object;

means for acquiring images of the calibration object;

means far moving the device with respect to the calibration object;

means for performing a series of acquisitions, each acquisition being associated to a calibration position of the device;

means for determining projection parameters associated to each calibration position of the device based on the acquisitions performed; and means for an additional position that has not been taken by the device during the acquisition to determine projection parameters values associated to this additional position according to the parameters associated to the calibration positions.

38. An apparatus for reconstructing a three dimensional model from acquired images comprising:

moans for emitting radiation;

means for providing a calibration object;

means for acquiring images of the calibration object;

means for moving the device wit respect to the calibration object;

means for providing an object to be imaged;

means for performing a series of acquisitions, each acquisition being associated to a calibration position of the device;

means for determining projection parameters associated to each calibration position of the device hued on the acquisitions performed;

means for an additional position that has not been taken by the device during the acquisition to determine projection parameters values associated to this additional position according to the parameters associated to the calibration positions; and means for reconstructing the three-dimensional model of the object from the images acquired and the associated projection parameters, determined during the calibration phase.

* * * * *

UNITED STATES PATENT AND TRADEMARK OFFICE
CERTIFICATE OF CORRECTION

PATENT NO. : 7,066,646 B2  
APPLICATION NO. : 10/737078  
DATED : June 27, 2006  
INVENTOR(S) : Pescatore et al.

It is certified that error appears in the above-identified patent and that said Letters Patent is hereby corrected as shown below:

Column 4:
Line 19, after "the" delete "x," and insert therefor --$x_1$--

Column 9:
Line 4, after "that" delete "ham" and insert therefro --has--

Column 10:
Line 12, after "device" delete "wit" and insert therefor --with--
Line 19, after "device" delete "hued" and insert therefor --based--

Signed and Sealed this

Fifth Day of December, 2006

JON W. DUDAS  
*Director of the United States Patent and Trademark Office*